United States Patent [19]

Sidorenko et al.

[11] 4,409,992

[45] Oct. 18, 1983

[54] ELECTRONIC ERGOMETER

[76] Inventors: Georgy I. Sidorenko, ulitsa Pulikhova, 7, kv. 37; Vladimir I. Stankevich, ulitsa Plekhanova, 32, korpus 2, kv. 84; Mikhail V. Sklema, ulitsa Matusevicha, 25, kv. 107; Arkady D. Margolin, ulitsa Kalinovskogo, 63, kv. 5, all of Minsk, U.S.S.R.

[21] Appl. No.: 197,756

[22] Filed: Oct. 16, 1980

[51] Int. Cl.$^3$ .............................................. A61B 5/10
[52] U.S. Cl. ............................ 128/782; 272/DIG. 6
[58] Field of Search ............................. 128/774, 782; 272/DIG. 6; 275/DIG. 5

[56] References Cited

U.S. PATENT DOCUMENTS

| | | | |
|---|---|---|---|
| 3,395,698 | 9/1968 | Morehouse | 272/DIG. 6 X |
| 3,767,195 | 10/1973 | Dimick | |
| 3,797,010 | 3/1974 | Adler | |
| 4,112,926 | 9/1978 | Schulman | |
| 4,117,834 | 10/1978 | McPartland | |
| 4,224,952 | 9/1980 | Sidorenko et al. | 128/782 |

FOREIGN PATENT DOCUMENTS 301534 of 0000 U.S.S.R. .
469053 of 0000 U.S.S.R. .

OTHER PUBLICATIONS

"Body Speedometer", JS & A Group, Inc., Catalog, p. 17.

*Primary Examiner*—Kyle L. Howell
*Assistant Examiner*—John C. Hanley
*Attorney, Agent, or Firm*—Lilling & Greenspan

[57] ABSTRACT

Disclosed is an electronic ergometer placed in a housing and comprising a series arrangement of a transducer, for converting the oscillations of the body center of gravity of an individual into an electrical signal and implemented as a seismic pickup, and a pulse shaper having its output connected to an adjustable high-frequency multivibrator with a frequency adjusting means. A frequency divider is connected to the output of the high-frequency multivibrator, the output of the frequency divider being connected to the counting inputs of a first multi-digit counter and a second multi-digit counter. The outputs of the first counter are connected to inputs of an indicator. The control input and one of the reset inputs of the second counter are connected to an adjustable timer, whose reset input is connected to a time interval adjusting unit. The outputs of the second counter are connected to the inputs of a power indication permitting unit, the outputs of which are connected to inputs of the indicator. The reset inputs of the frequency divider and of the first counter and a second reset input of the second counter are connected to a zero setting unit. The control inputs of the indicator and of the power indication permitting unit are connected to an indicator switching unit.

9 Claims, 20 Drawing Figures

ELECTRONIC ERGOMETER

FIELD OF THE INVENTION

The present invention relates to devices for registering loads exerted on an individual performing a movement, and more particularly to electronic ergometers.

The present invention can be used in medical scientific research, in medical practice, in sports, in curative physical culture exercises, in health resort service, and in space medicine.

BACKGROUND OF THE INVENTION

Routine physical exercise has long been extolled by virtually every medical authority as essential to good health and longevity. Because of modern conveniences and work-saving technology, the average person expends less physical energy today than did his counterparts in generations past. As a result, the current generation by and large does not get the physical exercise necessary for good health. Insufficient training of the human heart, as well as constantly increasing emotional stresses and inadequate physical loads, cause a steady increase in the number of people having cardiovascular disorders.

As far as lethality and invalidization of people are concerned, cardiovascular disorders come first in the world.

In recent years there has been an awakening to the need for a more systematized approach to the problem of exercise. Particularly, individuals in the over-thirty years age bracket are having routine exercise prescribed by their physicians as a preventive measure against heart disease and other associated cardiovascular disorders. Numerous recent publications have recognized a correlation between physical fitness and exercise and have delineated detailed regimens of programs of exercise intended to yield the desired results. The exercises must be performed only under medical suprvision in respect to physical loads and the physical activity of the individual.

DESCRIPTION OF THE PRIOR ART

Known in the art is a pedometer consisting of a seismic mass and a mechanical counter (cf. U.S.S.R. Author's Certificate No. 301,534). The operation of this pedometer is based on perception of the oscillations of the body center of gravity of a moving individual by the seismic mass. Each oscillation of the seismic mass is transmitted through a push rod to the mechanical counter which registers these oscillations. The pedometer counts all the oscillations of the individual in the vertical plane. This leads to false counts with the result that the counted number is somewhat greater than the actual number of steps.

Also known in the art is a pedometer for counting the number of steps performed by a walking or running person (cf. U.S.S.R. Author's Certificate No. 469,053) and having a housing which incorporates a series arrangement of a transducer for converting the oscillations of the body center of gravity of the person into an electrical signal, a pulse shaper, and an electrical signal counting/indicating unit. A power supply unit is connected to the pulse shaper and to the counting/indicating unit. The transducer is constituted by two pairs of contacts respectively disposed in the toe tip portion and in the heel portion of the insole of a shoe. These pairs of contacts are connected in parallel with each other and are closed at the moment the foot touches the ground (or a support) during walking or running. The counting/indicating unit is an electromechanical counter which is actuated at the time of application of a pulse from the output of the pulse shaper. When at least one pair of contacts of the transducer is closed, an accumulating element at the input of the pulse shaper is also closed with the result that redistribution of charges occurs and a current pulse is thus produced to actuate the pulse shaper which, in turn, also generates a pulse. The pulse causes the indicating/counting unit to change its reading.

The known pedometers are capable only of counting the number of steps performed by an individual and do not provide estimation of his physical activity. The number of steps is usually counted with poor accuracy, whereas the pedometers providing a higher accuracy require specially adapted footwear or wires to connect the transducer to the pulse shaper, which creates inconvenience when the pedometer is used.

Known in the art is a device for measuring and treating hyperactivity in human beings (cf. U.S. Pat. No. 4,112,926). This device comprises a plurality of sensors disposed in a horizontal plane at 120° to each other and connected to an electronic unit for estimating activity and hyperactivity of an individual. The electronic unit comprises monostable multivibrators connected to two binary counters. One of the counters is used for counting all movements, while the other, having a variable division factor, is used for estimating hyperactivity. The counter for estimating hyperactivity is connected to an adjustable timer. If the quantity of movements during a time period determined by the timer does not exceed the division factor of the counter, no signal is applied to the monostable multivibrator which controls the operation of an audible signalling device. If the quantity of movements performed by the individual during the predetermined time interval is above the division factor of the counter, the counter overflows and the signal from the output of the counter is applied to the monostable multivibrator which turns on the audible alarm alerting the individual to an excess in his activity level. The signals from the counters are also applied to a storage unit connected to a stationary digital indicator, which makes it possible to obtain digital data on the total quantity of movements and on the quantity of hyperactive movements upon cessation of the exercise. Such a device, however, estimates physical activity and hyperactivity and alerts the individual to excesses in his activity level irrespective of the rate at which a movement has been performed and of the work performed during this movement. Besides, such a device does not provide information on the quantity of the movements performed by the individual during a given time interval in digital form.

Known is a physiological motor activity monitoring apparatus (cf. U.S. Pat. No. 4,117,834). This apparatus includes a combination of modular devices in capsule form adapted to be worn on a person, e.g. with the aid of a watchband.

According to one embodiment of that invention the apparatus includes a combination of a motion detecting transducer, an accumulator incremented for $2^n$ number of movements and a 4-digit light-emitting diode display module for providing a visual signal that an allowed number of events has occurred.

An alternate embodiment of that invention comprises a motion detecting transducer, an accumulator incremented for $2^n$ number of movements in a selected accumulation interval, and a multi-cell random-access memory to which the contents of the accumulator are transferred and stored at the termination of each accumulation interval defined by a timer module, i.e., the time intervals of data accumulation are defined by the output pulse of a quartz crystal oscillator and frequency divider.

Such an apparatus is capable of detecting and storing a number of specific physiological events, as well as of alerting the person wearing the apparatus that a preset number of such events has occurred.

Such an apparatus, making it possible to determine the quantity of movements in a given interval, does not permit separation of the loads exerted on a person according to their intensities. Since the apparatus is to be worn on a watchband, the quantity of movements registered by the apparatus usually does not coincide with the physical energy expended by the person because a hand executes the maximum quantity of movements, yet the energy spent on these movements represents only a portion of all the physical energy expended by the person during movement.

Also known is a portable device for automatically counting and indicating the quantity of physical movements directly in "aerobic points" (cf. U.S. Pat. No. 3,797,010).

Such a device includes an electromechanical transducer, in the form of an accelerometer, which is capable of sensing each step taken by an exerciser while walking, running or jogging either in place or over a distance course. The accelerometer in conjunction with associated circuitry produces a train of electrical pulses which are used an an input of a computer. Preferably, the transducer may be a piezoelectric crystal having a cantilever weight for converting mechanical impulses to electric signals.

The device is designed to measure and indicate physical exercise achievements and performs, among others, the following functions: (1) accumulation of the number of steps taken by an exerciser so as to indicate distance travelled thereby; (2) accumulation of clock pulses corresponding to time (so as to indicate elapsed time); (3) measurement of the rate of steps taken by the exerciser and detection of whether such rate is less than, equal to, or greater than a predetermined threshold; (4) generation of a low frequency tone whenever the rate of steps taken by the exerciser falls below the threshold (representing a desired minimum rate of steps); (5) integration of the rate of steps over time so as to indicate aerobic points achieved by the exerciser (corresponding to performance thereof); and (6) generation of a high-frequency tone when a desired level of achievement of the exerciser has been reached.

Such a device, however, alerts the exerciser only after performance of a predetermined number of steps and is not capable of warning him that the preset admissible level of load is achieved.

All the devices described above, although taking into account the intensity of the performed movements, are incapable of automatic readjustment to the rate of exercise and only warn of deviation from a predetermined rate. That means that the person is not permitted to vary the movement speed at will but must adapt himself to the device or to readjust the device from time to time. All this causes inconveniences when such devices are used and does not allow the peson to vary the rate of movement over a wide range. Besides, none of said devices is capable of determining the work performed by a person during walking or running, which does not permit accurate estimation of the energy expended by the person while performing physical exercise.

Up to date tens of different types of electronic ergometers have been developed. One of them is described in U.S. Pat. No. 3,767,195 and makes it possible to estimate a permissible load level for a given individual. The operation of this ergometer is based on measurement of various physiological parameters of a person subjected to a physical strain. By changes in the rate of the heart's beat, by an electrocardiogram or reogram or by other physiological parameters obtained from a person, as well as by the magnitude of the load and the time period during which the person is subjected to the load, a physician can determine the reserve of physical loads for this person.

However, since veloergometers represent stationary arrangements and physical loads are determined in an indirect way from the obtained physiological parameters, which requires application of electrodes, it is not possible to determine the amount of work and power directly in domestic conditions. Besides, veloergometric tests produce emotional stresses which introduce substantial changes into the obtained data. In addition, running veloergometric tests require various special equipment, as well as service personnel such as a doctor or a highly trained nurse. This makes mass examinations and monitoring of physical activity difficult. By means of veloergometric tests it is possible to determine the physical reserve for a given individual. But there arises a necessity for monitoring physical exercise in everyday life. This is particularly important in the course of medical rehabilitation of patients. Such a monitoring is also necessary during athletic training or for checking physical loads during space flights.

Known in the art is an electronic ergometer capable of measuring and registering the work performed by an individual, and of producing a visual and an audible signal when a predetermined threshold is achieved (cf. U.S.S.R. Author's Certificate No. 628,756).

The operation of such an ergometer is based on conversion of the oscillations of the body center of gravity of an individual into an electrical signal, the duration of which is proportional to the amplitude of said oscillations. The ergometer comprises a housing which incorporates a series arrangement of a transducer, for converting the oscillations of the body center of gravity of an individual into an electrical signal, a pulse shaper, and an electrical signal counting/indicating unit coupled to the pulse shaper, the transducer being implemented as a seismic pickup and the counting/indicating unit being provided with a series arrangement of a multi-digit counter and an indicator. The ergometer further comprises an adjustable high-frequency multivibrator with a frequency adjusting means, the control input of the multivibrator being connected to the output of the pulse shaper, a unit for selecting the multivibrator frequency having its output coupled to the frequency adjusting means, a frequency divider having its counting input connected to the output of the multivibrator and its output connected to the counting input of the multi-digit counter, and a zero setting unit having its output connected to the reset inputs of the frequency divider and of the multi-digit counter.

In order to provide for checking the permissible magnitude of the work performed by an individual the ergometer further comprises a setting unit for setting the permissible magnitude of work performed by the individual, a comparison circuit having one plurality of inputs connected to the outputs of the multi-digit counter, another plurality of inputs connected to the outputs of the setting unit and an output connected to the enable inputs of the frequency divider and of the high-frequency multivibrator, and a low-frequency multivibrator having its input connected to the output of the comparison circuit and its output connected to one of the inputs of a mixer, the other input of the mixer being connected to the output of the high-frequency multivibrator and the output of the mixer being connected to the counting/indicating unit.

Such an ergometer is capable of measuring and registering the work performed by an individual and of producing an audible and a visual signal indicating exhaustion of the reserve when a predetermined threshold is achieved. Indication of the current magnitude of the performed work or of the achievement of the threshold is accomplished by a digital indicator built into the device. This provides for constant monitoring of the work performed by the individual, as well as for alerting him when the permissible amount of work is used up.

However, during physical exercise a person may exhaust his physical abilities not only by performed a great amount of work but also by performing a relatively small amount of it in a short time. Therefore a problem arises of simultaneously monitoring the amount of the performed work and the magnitude of the power developed by an individual while performing work.

SUMMARY OF THE INVENTION

It is an object of the present invention to provide an electronic ergometer capable of measuring the power developed by an individual while walking, running or jogging.

Another object of the present invention is to provide an electronic ergometer capable of measuring the power developed by an individual with due regard for the anthropometric data pertained to the moving individual (weight, height, the average length of step), as well as for the rate of movement.

Still another object of the present invention is to provide an electronic ergometer capable of establishing a permissible power threshold.

Still another object of the present invention is to provide an electronic ergometer capable of indicating (in digital, visual and audible form) the achievement of the permissible power threshold.

With these and other objects in view there is proposed an electronic ergometer having a housing which incorporates a series arrangement of a transducer, for converting the oscillations of the body center of gravity of an individual into an electrical signal, the transducer being implemented as at least one seismic pickup; a pulse shaper; an adjustable high-frequency multivibrator with a frequency adjusting means and having a control input connected to the output of the pulse shaper; a first frequency divider having its counting input coupled to the output of the adjustable high-frequency multivibrator and its output connected to the counting input of a first multi-digit counter, the outputs of which are connected to an indicator a zero setting unit having its output connected to the reset inputs of the first frequency divider and of the first multi-digit counter; and a power supply unit. The ergometer, according to the invention, further comprises a second multi-digit counter having its first reset input connected to the output of the zero setting unit and its counting input connected to the output of the first frequency divider; an adjustable timer having its output connected to the control input and to a second reset input of the second multi-digit counter; a time interval adjusting unit having its output connected to the reset input of the adjustable timer; a power indication permitting unit having its inputs connected to the outputs of the second multi-digit counter and its outputs connected to the inputs of the indicator; and an indicator switching unit having its output connected to the control input of the indicator and to the control input of the power indication permitting unit.

Introduction of the adjustable timer allows to determination of the magnitude of the work performed by the individual during a given period of time, i.e., to obtain the magnitude of power. Introduction of the second multi-digit counter, of the power indication permitting unit and of the indicator switching unit allows to converting the magnitude of power into binary code for subsequent indication in digital form by the indicator.

It is expedient that the electronic ergometer further comprises a second frequency divider having its counting input connected to the output of the first frequency divider and to the counting input of the second multi-digit counter, its reset input connected to the output of the zero setting unit and its output connected to the counting input of the first multi-digit counter.

Introduction of the second frequency divider between the first frequency divider and the first multi-digit counter ensures a higher accuracy of the power measurements, because the first frequency divider develops at its output a pulse equivalent of 1 m-kgf of work, while the second frequency divider develops at its output a pulse equivalent of 100 m-kgf.

It is expedient that the electronic ergometer further comprises a register having its reset input connected to the output of the zero setting unit, its information inputs connected to the outputs of the second multi-digit counter and its outputs respectively connected to the inputs of the power indication permitting unit; and a peak power comparison circuit, for comparing the peak power developed by the individual with a permissible magnitude, having a first set of inputs connected to the outputs of the second multi-digit counter, a second set of inputs connected to the outputs of the register and an output connected to the control input of the register.

Introduction of the register and of the peak power comparison circuit provides comparsion between the power developed at a given moment and the maximum power developed during the previous measurements, and storage of the greatest magnitude. This is a valuable asset because the power developed by an individual varies over a wide range, while only the maximum magnitude of power is important.

The electronic ergometer may also include: a work comparison circuit, for comparing the work performed by the individual with a permissible magnitude, having a first set of inputs connected to the highest order bit position outputs of the first multi-digit counter; a setting unit, for setting the permissible magnitude of work performed by the individual, having its outputs connected to a second set of inputs of the work comparison circuit; a low-frequency multivibrator; and a mixer having its inputs respectively connected to the output of the low-frequency multivibrator and to the output of the adjustable high-frequency multivibrator and its output connected to the signal input of the indicator. It is expedient to employ a power comparison circuit, for comparing the power developed by the individual with a permissible magnitude, having a first set of inputs connected to the outputs of the second multi-digit counter; another setting unit, for setting the permissible magnitude of power developed by the individual, having its outputs connected to a second set of inputs of the power comparison circuit; and an OR gate having its inputs respectively connected to the output of the power comparison circuit and to the output of the work comparison circuit and its output connected to the enable input of the adjustable high-frequency multivibrator, to the enable input of the frequency divider and to the input of the low-frequency multivibrator.

Introduction of the power comparison circuit, of the power setting unit and of the OR gate provides for generating a warning signal in case the developed power reaches the permissible magnitude.

It is expedient that the electronic ergometer further comprises a second OR gate having its first input connected to the output of the indicator switching unit, its second input connected to the output of the power comparison circuit and its output connected to the control input of the power indication permitting unit.

Introduction of the second OR gate connected between the power comparison circuit and the indicator switching unit provides automatic indication of the power magnitude upon achievement of the permissible threshold.

Preferably, the seismic pickup in the electronic ergometer is a reed switch.

Such a seismic pickup permits obtaining a signal at its output, the value of which agrees with the values of the signals in the ergometer output circuit.

The aforementioned and other objects and advantages of the present invention will become more apparent upon consideration of the following detailed description of the preferred embodiments taken in conjunction with the accompanying drawings.

DETAILED DESCRIPTION OF THE INVENTION

The proposed ergometer 1 (FIG. 1) is installed in a housing 2 and is arranged on a subject 3 to be examined, i.e. on an individual. The oscillations of the body center of gravity of the individual act on a transducer 4 (FIG. 2) adapted for converting the oscillations of the body center of gravity into an electrical signal and including a seismic pickup. The output of the seismic pickup of the transducer 4 is connected to the input of a pulse shaper 5. The pulse shaper 5 may be, for example, a threshold element. The output of the pulse shaper 5 is connected to the control input of an adjustable high-frequency multivibrator 6 having a frequency adjusting means 7. The frequency adjusting means 7 may be, for example, a variable resistor or a variable capacitor.

Figure 2:
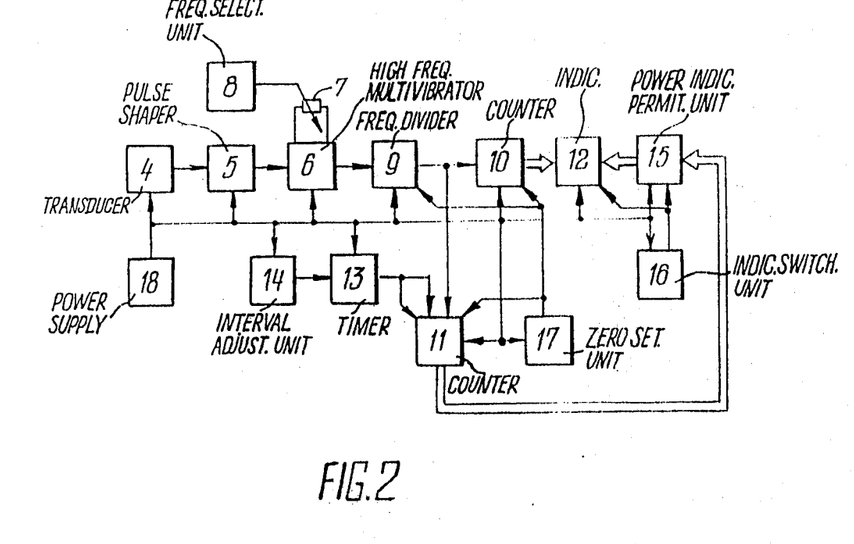
FIG. 2 is a block-diagram of the electronic ergometer, according to the invention.

The frequency adjusting means 7 is mechanically connected to a frequency selecting unit 8 which may be constituted by a set of switches (not shown).

The output of the adjustable high-frequency multivibrator 6 is connected to the counting input of a frequency divider 9 which is a multi-digit binary counter. The frequency divider 9 is provided with a reset input and an output. The output of the frequency divider 9 is connected to the counting input of a multi-digit counter 10 and to the counting input of a multi-digit counter 11. The counters 10 and 11 are multi-digit binary counters. The counter 10 is further provided with a reset input and a plurality of outputs equal in number to the number of bit positions of the counter 10.

The multi-digit counter 11 is further provided with a control input, two reset inputs and a plurality of outputs equal in number to the number of bit positions of the counter 10.

The ergometer 1 (FIG. 1) comprises an indicator 12 (FIG. 2) having a control input and information inputs one set of information inputs being connected to corresponding outputs of the multi-digit counter 10.

The control input and one of the reset inputs of the counter 11 are connected to the output of an adjustable timer 13 which is a pulse circuit. The duration of the output signal of the timer 13 is adjusted with the aid of a time interval adjusting unit 14. The outputs of the counter 11 are connected to the inputs of a power indication permitting unit 15 which is constituted by a plurality of AND gates equal in number to the number of outputs of the counter 11. One of the inputs of each of the AND gates is connected to the corresponding output of the counter 11, the other input of each of the AND gates being connected to the corresponding output of an indicator switching unit 16.

The indicator switching unit 16 is a threshold circuit controlled by a push-button (not shown).

The control input of the indicator 12 is connected to the output of the indicator switching unit 16, and the information inputs of a second set of inputs of the indicator 12 are connected to corresponding outputs of the power indication permitting unit 15.

Setting of the ergometer to zero is achieved with the aid of a zero setting unit 17 which is a one-shot circuit with a controlling push-button (not shown). The output of the zero setting unit is connected to the reset inputs of the frequency divider 9 and the counter 10 and to the second reset input of the counter 11.

The ergometer 1 is supplied from an independent power supply unit 18 connected to the transducer 4, to the pulse shaper 5, to the multivibrator 6, to the frequency divider 9, to the counters 10 and 11, to the indicator 12, to the timer 13, to the time interval adjusting unit 14, to the power indication permitting unit 15, to the indicator switching unit 16, and to the zero setting unit 17.

Figure 3:
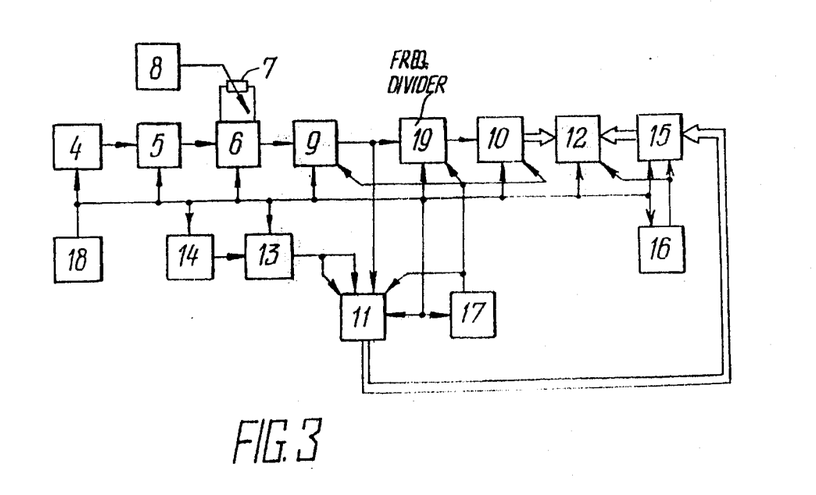
FIG. 3 is a block-diagram of the electronic ergometer, according to one of the embodiments of the invention.

FIG. 3 shows one of the embodiments of the ergometer 1 (FIG. 1) which further comprises a frequency divider 19 (FIG. 3) having its counting input connected to the output of the frequency divider 9 and to the counting input of the counter 11 and its reset input connected to the output of the zero setting unit 17. The output of the frequency divider 19 is connected to the counting input of the counter 10.

The frequency divider 19 is connected to the output of the power supply unit 18.

The frequency divider 19 is a multi-digit counter.

Figure 4:
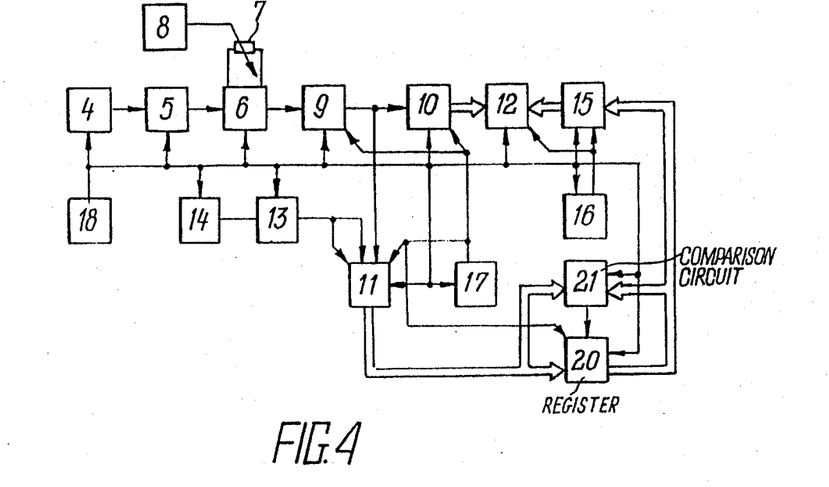
FIG. 4 is a block-diagram of the electronic ergometer, according to another embodiment of the invention.

FIG. 4 shows another embodiment of the ergometer 1 (FIG. 1) which comprises a register 20 (FIG. 4) having a control input, a reset input, and a plurality of information inputs equal in number to the number of the outputs of the register 20; and a peak power comparison circuit 21, for comparing the peak power developed by the individual with a permissible magnitude, and having a first set of inputs equal in number to the number of outputs of the counter 11, a second set of inputs equal in number to the number of outputs of the register 20 and an output.

The corresponding inputs of the register 20 are respectively connected to the corresponding outputs of the counter 11, and reset input of the register 20 is connected to the output of the zero setting unit 17. The corresponding outputs of the register 20 are respectively connected to the corresponding inputs of the power indication permitting unit 15, and to the corresponding inputs of the first set of inputs of the comparison circuit 21. The control input of the register 20 is connected to the output of the comparison circuit 21.

The corresponding inputs of the second set of inputs of the comparison circuit 21 are respectively connected to the corresponding outputs of the counter 11.

The register 20 and the comparison circuit 21 are connected to the output of the power supply unit 18.

Figure 5:
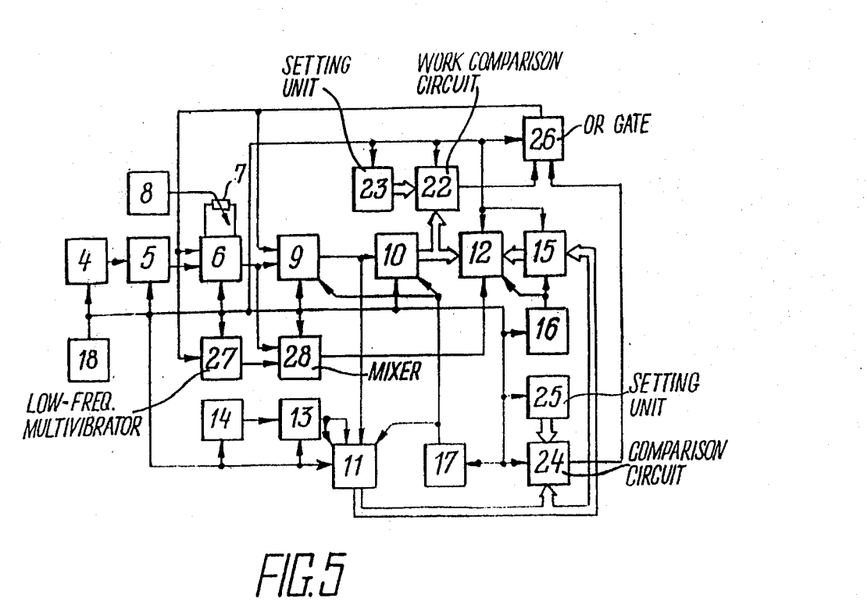
FIG. 5 is a block-diagram of the electronic ergometer, according to still another embodiment of the invention.

FIG. 5 shows still another embodiment of the ergometer 1 (FIG. 1) which comprises a work comparison circuit 22 (FIG. 5), for comparing the work performed by the individual with a permissible magnitude, having a first set of inputs respectively connected to the corresponding highest order bit position outputs of the counter 10 and a second set of inputs respectively connected to the corresponding outputs of a setting unit 23 for setting the permissible magnitude of work.

The setting unit 23 is a pulse circuit with switches (not shown). The binary code at the output of the setting unit 23 depends on the position of the switches.

The ergometer shown in FIG. 5 further comprises a power comparison circuit 24, for comparing the power developed by the individual with a permissible magnitude, having an output and two sets of inputs, the inputs of each set being equal in number to the number of outputs of the counter 11.

The inputs of the first set of inputs of the comparison circuit 24 are respectively connected to the corresponding outputs of the counter 11, the inputs of the second set are respectively connected to the corresponding outputs of a setting unit 25 for setting the permissible magnitude of power, and the output of the comparison circuit 24 is connected to the first input of an OR gate 26, whose second input is connected to the output of the comparison circuit 22. The output of the OR gate 26 is connected to the enable input of the frequency divider 9, to the enable input of the multivibrator 6 and to the input of a low-frequency multivibrator 27 whose output is connected to one of the inputs of a mixer 28. The other input of the mixer 28 is connected to the output of the multivibrator 6, the output of the mixer 28 being connected to the signal input of the indicator 12.

The mixer 28 is a two-input AND gate.

The comparison circuit 22, the setting unit 23, the comparison circuit 24, the setting unit 25, the OR gate 26, the multivibrator 27 and the mixer 28 are connected to the power supply unit 18.

Figure 6:
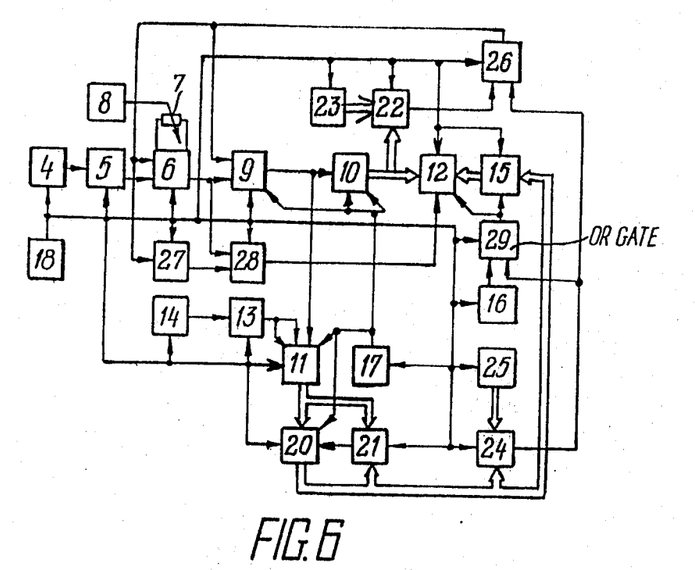
FIG. 6 is a block-diagram of the electronic ergometer, according to still another embodiment of the invention.

FIG. 6 shows still another embodiment of the ergometer 1 (FIG. 1) which comprises an OR gate 29 (FIG. 6) having one input connected to the output of the indicator switching unit 16, a second input connected to the output of the comparison circuit 24 and an output connected to the control input of the power indication permitting unit 15 and to the control input of the indicator 12. The OR gate 29 is further connected to the power supply unit 18.

To obtain data on work performed by the individual and on power developed by him, with the body center of gravity of the individual oscillating in relation to three planes, the transducer 4 (FIG. 7) includes three seismic pickups 30, 31 and 32. In such a case the pulse shaper 5 comprises three threshold elements 33, 34 and 35 having their inputs respectively connected to the seismic pickups 30, 31 and 32. The outputs of the threshold elements 33, 34 and 35 are connected to the inputs of an adder 36 which is an OR gate. The number of inputs of the adder 36 is equal to the number of threshold elements. The output of the adder 36 constitutes the output of the pulse shaper 5 and is connected to the control input of the multivibrator 6.

Figure 7:
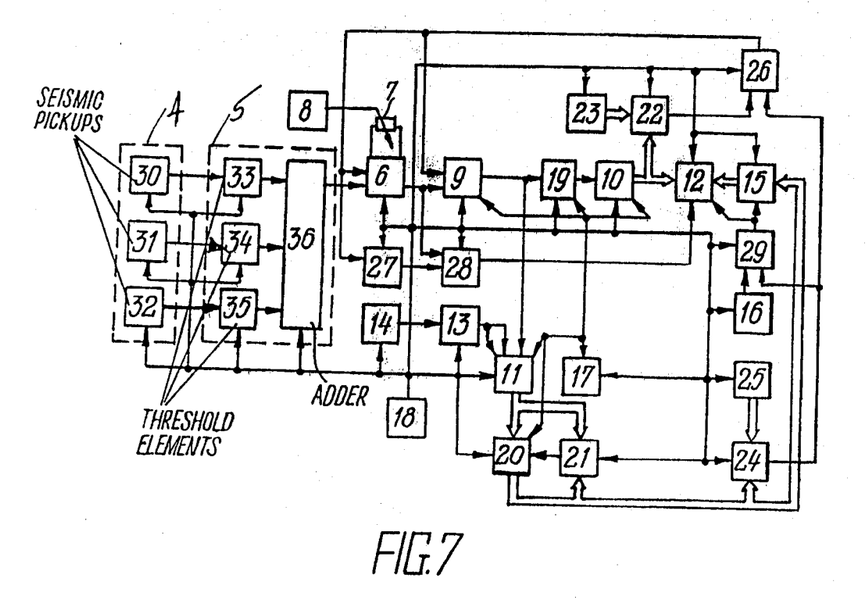
FIG. 7 is a block-diagram of the electronic ergometer, according to still another embodiment of the invention.

The seismic pickups 30, 31 and 32, the threshold elements 33, 34 and 35 and the adder 36 are connected to the power supply unit 18.

A seismic pickup of the transducer 4 (FIGS. 2-7) may be constituted by a reed switch 37 (FIG. 8) and a seismic mass 38 which is a permanent magnet secured to a lever 39 and connected to the housing 2 (FIG. 1) by means of elastic elements 40 (FIG. 8) and by an axis 41.

The electronic ergometer (FIG. 1) operates as follows.

Figure 1:
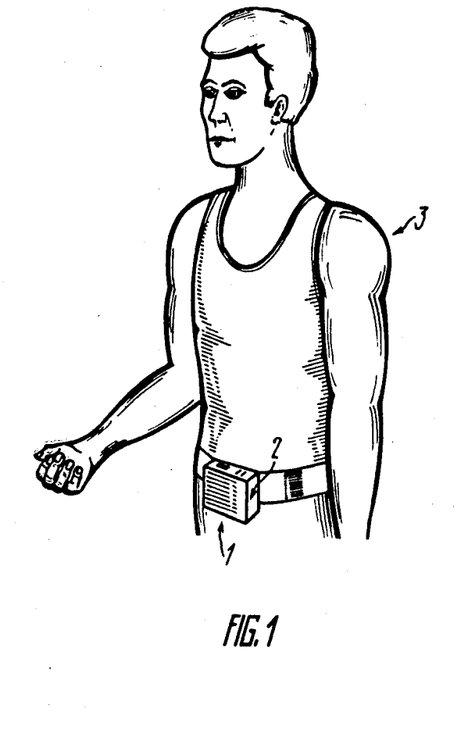
FIG. 1 shows how the electronic ergometer is arranged on an individual, according to the invention.

The housing 2 of the ergometer 1 is attached to the waist-band of the individual.

The operation of the ergometer is based on conversion of the oscillations of the body center of gravity of the individual into an electrical signal, the duration of which is proportional to the amplitude of these oscillations.

Figure 8:
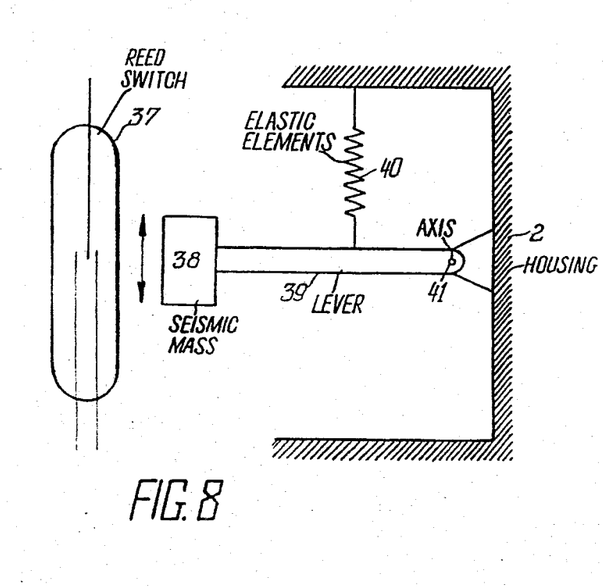
FIG. 8 shows a seismic pickup constituted by a reed switch, according to the invention.
Figures 9A, 9B, 9C:
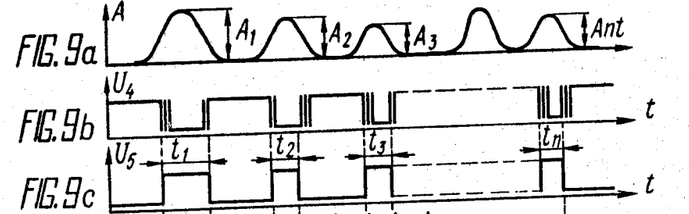
FIGS. 9a–9l are diagrams showing variations of the amplitude of the oscillations acting on the seismic pickup and variations of the voltages at the outputs of the units constituting the electronic ergometer, according to the invention.

During walking, running or jogging the body center of gravity of the individual performs oscillatory motions (FIG. 9a) which are transmitted to the seismic mass 38 (FIG. 8). Under the influence of these motions the seismic mass 38 oscillates on elastic elements 40 around the axis 41 and along the reed switch 37. When the seismic mass 38 enters the actuation zone of the switch 37, the contacts of the switch 37 are switched over and the input of the pulse shaper 5 (FIG. 2) is supplied with a signal $U_4$ (FIG. 9b). The electrical signal from the seismic pickup of the transducer 4 (FIG. 2) modulates the high-frequency output of the multivibrator 6. The repetition rate of the pulses developed by the multivibrator 6 is set by means of the frequency adjusting means 7 and of the frequency selecting unit 8 in accordance with the specific data pertaining to the individual, such as weight, height, the average length of step, as well as with the average rate of movement. The frequency divider 9 produces a pulse equivalent of 100 m-kgf.

The calculation of the work performed by individuals having different weight, height and other different characteristics gives a magnitude of the work per step ranging from 8 to 30 m-kgf. If a 10 m-kgf unit is chosen for the calculation, the magnitudes of the performed work per step represented by whole numbers, for example, 16 and 23 m-kgf, cannot be obtained in each case. One the other hand, a 100 m-kgf unit causes an increased discreteness and, therefore, greater measurement errors. The decimal number system, which is most habitual for human beings, was selected to represent the measurement results.

The pulses produced by the frequency divider 9 are counted by the multi-digit counter 10 and are displayed by the indicator 12. The same pulses from the output of the frequency divider 9 are counted by the multi-digit counter 11 over a time period determined by the timer 13. The magnitude of power may be seen on the digital display of the indicator 12 upon pressing the push-button (not shown) of the indicator switching unit 16. In this case the signal corresponding to the magnitude of the power developed by the individual via the power indication permitting unit 15 is applied to the indicator 12 and is indicated on its display.

Figures 9D, 9E:
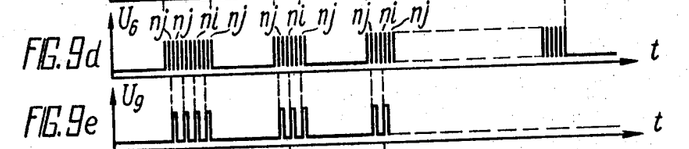

After the power supply unit 18 is turned on, the counters 10 and 11 and the frequency divider 9 are automatically set to zero by the signal delivered from the output of the zero setting unit 17. During movement (walking, running or jogging) the individual performs oscillatory motions. The amplitude of oscillations of the body center of gravity of the individual depends on his peculiarities including his walk, and amounts, on the average, to 3 to 4 cm. These oscillations are transmitted, via the housing 2 (FIG. 1), to the ergometer 1. The transducer 4 (FIG. 2) converts the amplitude A of the body center of gravity into an electrical signal $U_4$ (FIGS. 9a and 9b). This signal is applied from the output of the pickup of the transducer 4 (FIG. 2) to the input of the pulse shaper 5. The pulses $U_5$ (FIG. 9c) from the output of the pulse shaper 5 (FIG. 2) are delivered to the control input of the multivibrator 6. The duration of the pulses $U_5$ (FIG. 9c) is proportional to the amplitude of the body center of gravity of the individual ($t_1 \sim A_1$, $t_2 \sim A_2$, $t_3 \sim A_3$, $t_n \sim A_n$). At the instant when a pulse is applied to the control input of the multivibrator 6 (FIG. 2), the multivibrator 6 produces a high-frequency signal. Thus, the multivibrator 6 provides at its output pulse trains $U_6$ (FIG. 9d), the number of the pulses in the pulse train depending on the width of the control pulse and on the frequency to which the multivibrator 6 (FIG. 2) is adjusted.

The frequency of the pulses $U_6$ (FIG. 9d) at the output of the mulitvibrator 6 (FIG. 2) depends on the resistance of the frequency adjusting means 7 and is selected by means of the frequency selecting unit 8. The switches (not shown) of the frequency selecting unit 8 are set in accordance with the magnitude of the work performed by the individual during one step. This magnitude depends on the person's weight, height, average length of step, average rate of movement and amounts, on the average, to 8 to 30 m-kgf.

For each individual, the work performed during one step is calculated by using appropriate tables, monograms or a formula. The formula is derived on the basis of a known method providing determination of work performed by the kinematic links (hands and legs) of the individual by summing the magnitudes of work performed by each link. The above tables or monograms contain the values of the abovedescribed characteristics of different individuals. With these values selected for an individual, it is possible to determine the magnitude of the work which he performs during one step. This magnitude is introduced into the ergometer by operating the switches of the frequency selecting unit 8. The frequency selecting unit 8 provides selection of the frequency of the multivibrator 6 in a range between 3.36 and 12.6 kHz.

The frequency of the multivibrator 6 is selected depending on the magnitude of the work performed by the individual in a range between 8 and 30 m-kgf. The pulse trains from the output of the multivibrator 6 are applied to the counting input of the frequency divider 9. The division factor of the frequency divider 9, which is equal to $2^{12}$ (4096), and the adjustment range of the multivibrator frequency are selected so as to provide a higher accuracy in calculating the work performed by the individual. With the 4096 th ($n_i$th in FIG. 9d) pulse applied to the input of the frequency divider 9, the frequency divider 9 produces at its output a pulse $U_9$ (FIG. 9e) which is equivalent of 100 m-kgf. The pulses are counted by the counter 10 (FIG. 2) and are displayed by the indicator 12. Simultaneously the pulses $U_9$ (FIG. 9e) are applied to the counting input of the counter 11 (FIG. 2) which counts the work performed by the individual during a time interval determined by the timer 13, with the result that a binary code appears at the outputs of the counter 11, which corresponds to the average power developed by the individual during the time interval determined by the timer 13.

This time interval is set by means of the switch (not shown) of the time interval adjusting unit 14. The duration of the time interval is chosen equal to 1 sec., 10 sec., 1 min. or to any other value, according to the purpose for which the power developed by the individual is determined.

Figure 9F:
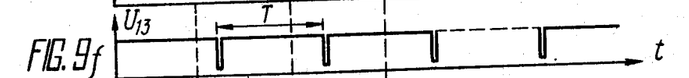

The timer 13 produces at its output an electrical signal $U_{13}$ (FIG. 9f) which is a sequence of pulses having width equal to the chosen time interval T set by the switch of the time interval adjusting unit 14 (FIG. 2). The signal $U_{13}$ (FIG. 9f) passes to the control input of the counter 11 (FIG. 2) which determines the average power taken over the time T. The same signal $U_{13}$ (FIG. 9f) appears at the reset input of the counter 11 (FIG. 2) resetting the counter 11. During the next time interval T the counter 11 determines a new magnitude of power. The counter 11 is reset during the time period between the pulses corresponding to the time intervals T and therefore said time period is chosen less than the duration of the signal $U_9$ (FIG. 9e) so as to provide a higher accuracy of the power measurements.

The binary code from the outputs of the counter 11 (FIG. 2) is applied to the inputs of the power indication permitting unit 15, the outputs of which are connected to the information inputs of the indicator 12. If it is necessary to read from the display of the indicator 12 the average magnitude of power developed by the individual during a chosen interval, the push-button of the indicator switching unit 16 is pressed. Then the signal from the output of the indicator switching unit 16 is applied to the control inputs of the power indication unit 15 and of the indicator 12. When this signal appears at the control input of the unit 15, the unit 15 permits the binary code from the output of the counter 11 to pass to the information inputs of the indicator 12. When this signal appears at the control input of the indicator 12, the indicator 12 stops indicating the magnitude of work and begins to indicate the magnitude of power. The duration of the signal at the output of the indicator switching unit 16 is equal to the time for which the push-button is pressed. Thus the time period during which the indicator 12 indicates power is equal to the time period during which the push-button is pressed so that the indication of power takes place only while the push button is pressed. As soon as the push-button is released, the indicator 12 again indicates the magnitude of work.

When the ergometer is no longer used, the power supply unit 18 is switched off, and the frequency divider 9, as well as both the counters 10 and 11, loose all the information stored therein.

During measurement of power it may be necessary to determine it in a short time interval, e.g. during 1 or 10 sec. However, since the work performed by an individual during one step has a minimum value of 5 to 8 m-kgf and the time duration of a step is commensurable with the interval of 1 sec., in such cases the performed work should be measured to an accuracy of 1 m-kgf, instead of 100 m-kgf as was the case during work measurements.

Therefore, to provide measurements of power in short time intervals, the ergometer 1 (FIG. 1) further comprises another frequency divider 19 (FIG. 3). The frequency divider 19 has a division factor equal to 100 in order to provide an output pulse equivalent of 100 m-kgf. This division factor is chosen so that, with a given frequency of the high-frequency multivibrator 6, the signal at the output of the frequency divider 9 is equivalent of 1 m-kgf for a given type of individual.

In such a case the ergometer operates as follows.

Figure 9G:
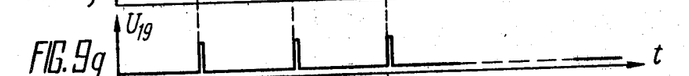

The output signal of the high-frequency multivibrator 6 is modulated by the signal $U_5$ (FIG. 9c), the duration of which is proportional to the amplitude of oscillations of the body center of gravity of the individual. The train of pulses from the output of the multivibrator 6 (FIG. 3) is applied to the counting input of the frequency divider 9, which, upon arrival of the $n_j$th pulse (FIG. 9d), produces at its output a pulse $U_9$ (FIG. 9e) equivalent of 1 m-kgf. The pulse $U_9$ simultaneously passes to the counting inputs of the frequency divider 19 and of the counter 11 (FIG. 3). After application of a hundred pulses, i.e. upon application of the $n_i$th pulse to the input of the frequency divider 19 from the output of the frequency divider 9, the input of the counter 10 is supplied with a pulse $U_{19}$ (FIG. 9g) equivalent of 100 m-kgf. Then the operation of the ergometer during measurement of work is the same as described above.

The pulses $U_9$ (FIG. 9e) appear at the counting input of the counter 11 (FIG. 3) simultaneously with their application to the input of the frequency divider 19. During time interval T set by the timer 13 the counter 11 determines the magnitude of the work performed during said time interval, i.e., provides measurement of power to a high accuracy. Thereupon the operation of the ergometer during measurement of power is the same as described above.

The ergometer described above provides for indication of only the current magnitude of power. Very often, however, it is necessary to know not power in general but the maximum power developed by an individual during the intervals of measurement, or the so-called peak power.

The ergometer adapted for measuring peak power further comprises a register 20 (FIG. 4) and a comparison circuit 21 for comparing the peak power developed by the individual with a pemissible magnitude.

Such an ergometer operates as follows.

The magnitude of power corresponding to the current time interval is written in binary code into the counter 11 and into the register 20. During the next time interval T peak power is measured by the counter 11 and the measured value is simultaneously applied to the inputs of the register 20 and of the first set of inputs of the comparison circuit 21. The inputs of the second set of inputs of the comparison circuit 21 are supplied from the outputs of the register 20 with the binary code stored in the register 20 and corresponding to the peak value reached by power during one of the previous time intervals T. If the peak power magnitude stored in the register 20 is greater than, or equal to, the peak power corresponding to the current time interval, the peak power magnitude stored in binary code in the register 20 remains therein. The signals corresponding to this magnitude of peak power are also applied to the inputs of the power indication permitting unit 15 so that the peak power magnitude may be read from the indicator display as described above.

If the peak power corresponding to the current time interval is greater than the peak power written into the register 20 during one of the previous time intervals, the comparison circuit 21 develops a control signal applied to the register 20. Upon application of the control signal the new magnitude of peak power is written into the register 20. Thus the register 20 stores the maximum value of peak power developed by the individual during the previous time intervals. By the use of the power indication permitting unit 15 and of the indicator switching unit 16 the maximum value of peak power may be read from the indicator display as described above.

During monitoring of the physical activity of cardiac patients in the course of medical rehabilitation it is necessary to limit excessive physical activity of such patients.

The operation of the erogometer during monitoring and indication of the achievement of the permissible magnitudes of work and power is as follows.

Prior to operation, the switches (not shown) of the permissible work magnitude setting unit 23 (FIG. 5) and of the permissible power magnitude setting unit 25 are switched to set the magnitudes of work and power permissible for a given individual. According to the position of the switches the units 23 and 25 develop at their outputs binary codes respectively corresponding to the permissible magnitudes of work and power.

The codes from the outputs of the units 23 and 25 are respectively applied to the inputs of the second set of inputs of the comparison circuit 22 and of the second set of inputs of the comparison circuit 24. The inputs of the first set of inputs of the comparison circuit 22 are supplied with the binary code from the outputs of the counter 10, and the inputs of the first set of inputs of the comparison circuit 24 are supplied with the binary code from the outputs of the counter 11.

When the amount of work is calculated, the counting unit of the counter 10 is supplied with pulses $U_9$ (FIG. 9e) from the output of the frequency divider 9 (FIG. 5). If the binary code at the outputs of the counter 10, which corresponds to the magnitude of the performed work, coincides with the binary code at the output of the setting unit 23, which corresponds to the magnitude of work permissible for the individual, the comparison circuit 22 develops a coincidence signal delivered to one of the inputs of the OR gate 26. The other input of the OR gate 26 is supplied with a coincidence signal when the magnitude of the developed peak power equals the permissible magnitude of peak power.

Figure 9H:
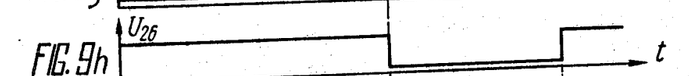
Figure 9I:
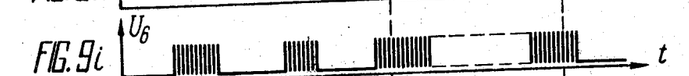
Figure 9J:
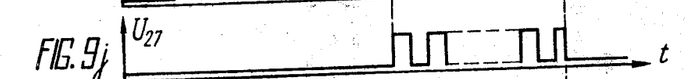

Upon application of a coincidence signal to an input of the OR gate 26, the OR gate 26 develops at its output a signal $U_{26}$ "Reserve used up" (FIG. 9h). This signal passes to the enable input of the frequency divider 9 (FIG. 5) switching it off, to the enable input of the high-frequency multivibrator 6 switching it into continuous operation (see FIG. 9i) and to the input of the low-frequency multivibrator 27 permitting its operation (see FIG. 9j).

Figure 9K:
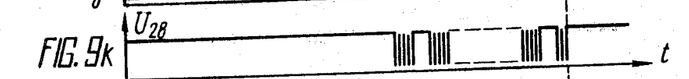

The signal $U_6$ (FIG. 9i) from the output of the multivibrator 6 (FIG. 5) and the signal $U_{27}$ (FIG. 9j) from the output of the multivibrator 27 (FIG. 5) are applied to the inputs of the mixer 28 which is a two-input AND gate. The mixer 28 develops at its output pulse trains $U_{28}$ (FIG. 9k), the repetition frequency of the pulse trains $U_{28}$ being the same as the frequency of the signals produced by the multivibrator 27 (FIG. 5), while the repetition frequency of the pulses in the pulse trains is the same as the frequency of the signals produced by the multivibrator 6. The signal from the output of the mixer 28 is applied to the signal input of the indicator 12.

Upon application of the signal $U_{28}$ (FIG. 9k) to the indicator 12 (FIG. 5) the ergometer produces an intermittent sound signal and the digital display of its indicator blinks. The intermittent sound signal and the blinking of the display attracts the attention of the individual warning him that his working capacity is used up, i.e., that he has exceeded the permissible magnitude of work or power, depending on the input of the OR gate 26 which is supplied with a coincidence signal. If the permissible magnitude of work is reached, the digital value indicated by the indicator 12 corresponds to the permissible magnitude of work. When the permissible magnitude of power is reached, the indicator 12 indicates the work performed by the individual, the achieved magnitude of power in that case may be read by pressing the push-button of the indicator switching unit 16, whereupon the indicator display shows the permissible magnitude of power achieved by the individual.

Figure 9L:
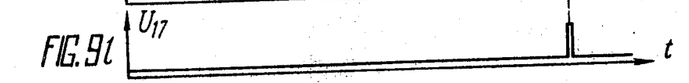

After receiving the signal "Reserve used up" the individual must stop moving and have a rest. Upon pressing the "Zero setting" push-button the zero setting unit 17 produces a pulse $U_{17}$ (FIG. 9l) which causes the sound signal and the blinking of the indicator 12 (FIG. 5) to cease. The same signal $U_{17}$ (FIG. 9l) resets the frequency divider 9 (FIG. 5) and the counter 10 and 11 with the result that the ergometer returns to the initial state.

When the ergometer shown in FIG. 5 is used, the individual himself must determine which of the permissible magnitude is achieved when the signal "Reserve used up" is produced. The block-diagram of the ergometer automatically indicating which of the permissible magnitudes is achieved is shown in FIG. 6. Such an ergometer operates as follows.

The indication of the achieved magnitude of work is carried out as described above. If the individual, while performing work, has achieved the permissible magnitude of power, the coincidence signal from the output of the comparison circuit 24 is applied to one of the inputs of the OR gate 26 whereupon a sound signal is generated, as described above. Automatic digital indication of the permissible magnitude of power achieved by the individual is accomplished with the aid of the OR gate 29. The coincidence signal from the comparison circuit 24, simultaneously with its application to one of the inputs of the OR gate 26, appears at one of the inputs of the OR gate 29, the other input of which is connected to the output of the indicator switching unit 16. The signal from the output of the OR gate 29 is applied to the control inputs of the indicator 12 and of the power indication permitting unit 15. Upon application of the control signal to the indicator 12 and to the power indication permitting unit 15 (when the permissible magnitude of power is achieved or when the push-button of the indicator switching unit 16 is pressed) the indicator 12 stops indicating the magnitude of work and begins to indicate the magnitude of power which is transmitted through the power indication permitting unit 15. Thus the OR gate 29 permits automatic indication of the achievement of the permissible magnitude of work or power, depending on which of said magnitudes is achieved, as well as reading of the magnitude of peak power when the push-button of the indicator switching unit 16 is pressed. In all the other cases the indicator 12 indicates the magnitude of the performed work.

If it is necessary to register work and power with consideration for oscillations of the body center of gravity in all directions, the transducer 4 (FIG. 7) of the ergometer 1 (FIG. 1) is composed of three seismic pickups 30, 31 and 32 (FIG. 7). The seismic pickups respond to oscillations of the body center of gravity in three respective planes i.e., to movements upward of downward, forward or backward, to the left or to the right. If necessary, any number of pickups can be used. Each of the pickups 30, 31 and 32 is placed in the plane and along the axis of the oscillations to which this pickup should respond. The duration of the signal produced by the pickup 30, 31 or 32 is proportional to the amplitude A of oscillations of the body center of gravity in the corresponding plane (FIGS. 9a and 9b). The signals from the outputs of the pickups 30, 31 and 32 (FIG. 7) are respectively applied to the inputs of the threshold elements 33, 34 and 35, which are the inputs of the pulse shaper 5. The output signals of the threshold elements 33, 34 and 35 are applied to the inputs of the adder 36. The signal $U_5$ (FIG. 9c) from the output of the adder 36 (FIG. 7), which is the output of the pulse shaper 5, is applied to the control input of the multivibrator 6, the duration of this signal being proportional to the amplitude of oscillations of the center of gravity in a corresponding plane. Further operation of the ergometer having three pickups 30, 31 and 32 is similar to that described for the ergometer having a single pickup.

When the ergometer is used by cardiac patients, e.g., after they have had myocardial infarction, such patients may extend the range of their movements by keeping watch on the achievement of the permissible magnitudes of work and power. The ergometer makes it possible to extend the range of movement of cardiac patients during medical rehabilitation without increasing the risk of recurrence of mycardial infarction.

The ergometer can be used for determining labor requirements for some production processes and for measuring work and power in domestic conditions during walking, running or jogging. The ergometer also provides for estimation of the work performed by an athlete during training or competition, as well as for estimation of the power developed in such cases.

In all the above cases the ergometer can be used without preliminary setting of the permissible magnitude of work or power.

The ergometer is a portable device and can be carried by the exerciser himself.

While the invention is described herein in terms of the preferred embodiments, numerous modifications may be made without departure from the spirit and scope of the invention as defined in the appended claims.

We claim:

1. An electronic ergometer measuring work performed by an individual and power developed by said individual while performing work in terms of oscillation of the individual's body's center of gravity, comprising:
  a power supply unit having an output;
  transducer means converting the oscillations of the body center of gravity of said individual into an electrical signal provided as an output, said transducer means including at least one seismic pickup having an output;
  a pulse shaper comprising a threshold element and having a first input connected to said output of said power supply unit, a second input connected to said output of said transducer means, and an output;
  an adjustable high-frequency multivibrator having a control input connected to said output of said shaper, an input connected to said output of said power supply unit, and an output;
  frequency adjusting means operatively associated with said adjustable high-frequency multivibrator and setting the frequency of said output of said adjustable high-frequency multivibrator;
  frequency selecting means having an output connected to said frequency adjusting means and selecting the frequency of said adjustable high-frequency multivibrator;
  a first frequency divider having a counting input connected to said output of said adjustable high-frequency multivibrator, an input connected to said output of said power supply unit, a reset input, and an output;
  a first multi-digit counter having a set of bit position outputs equal in number to the number of bit positions of the counter, a counting input connected to said output of said first frequency divider, an input connected to said output of said power supply unit, a reset input, and an output;
  an indicator having a control input, a first set of inputs and a second set of inputs being respectively connected to corresponding bit position outputs of said first multi-digit counter;
  a zero setting unit having an input connected to said output of said power supply unit, and an output connected to said reset input of said first frequency divider and to said reset input of said first multi-digit counter;
  a second multi-digit counter having a set of bit position outputs equal in number to the number of bit positions of the counter, a counting input connected to said output of said first frequency divider, a first reset input connected to said output of said zero setting unit, an input connected to said output of said power supply unit, a second reset input, and a control input;
  an adjustable timer having an input connected to said output of said power supply unit, an output connected to said second reset input and to said control input of said second multi-digit counter, and a reset input;
  a time interval adjusting unit having an input connected to said output of said power supply unit, and an output connected to said reset input of said adjustable timer;
  a power indication permitting unit having a control input, a set of inputs equal in number to the number of bit positions of said second multi-digit counter, a set of outputs equal in number to the number of inputs of said set of inputs, and an input connected to said output of said power supply unit, the inputs of said set of inputs being respectively connected to corresponding bit position outputs of said second multi-digit counter, and the outputs of said set of outputs being respectively connected to corresponding inputs of said second set of inputs of said indicator;
  an indicator switching unit having an input connected to said output of said power supply unit, and an output connected to said control input of said indicator and to said control input of said power indication permitting unit; and
  a housing accommodating said transducer means, said pulse shaper, said adjustable high-frequency multivibrator, said first frequency divider, said frequency adjusting means, said frequency selecting unit, said first multi-digit counter, said indicator, said second multi-digit counter, said adjustable timer, said time interval adjusting unit, said zero setting unit, said power indication permitting unit, said indicator switching unit, and said power supply unit.

2. An electronic ergometer according to claim 1, further comprising a second frequency divider having a counting input, a reset input, an input and an output, said counting input being connected to said output of said first frequency divider and to said counting input of said second multi-digit counter, said reset input being connected to said output of said zero setting unit, said input being connected to said output of said power supply unit, and said output being connected to said counting input of said first multi-digit counter.

3. An electronic ergometer according to claim 1, further comprising:
  a register having an input, a control input, a reset input, a set of information inputs equal in number to the number of outputs of said plurality of outputs of said second multi-digit counter and a set of outputs equal in number to the number of bit positions of the register, said input being connected to said output of said power supply unit, said reset input being connected to said output of said zero setting unit, the inputs of said set of information inputs being respectively connected to corresponding bit position outputs of said second multi-digit counter, and the outputs of said set of outputs being respectively connected to corresponding inputs of said set of inputs of said power indication permitting unit; and a peak power comparison circuit comparing the peak power developed by said individual with a permissible magnitude and having an input, a first set of inputs equal in number to the number of bit position outputs of said second multi-digit counter, a second set of inputs equal in number to the number of said outputs of said set of outputs of said register, and an output, said input being connected to said output of said power supply unit, the inputs of said first set of inputs being respectively connected to corresponding bit position outputs of said second multi-digit counter, the inputs of said second set of inputs being respectively connected to corresponding outputs of said set of outputs of said register, and said output being connected to said control input of said register.

4. An electronic ergometer according to claim 1, wherein said seismic pickup includes a reed switch having an output connected to said input of said pulse shaper.

5. An electronic ergometer according to claim 1, wherein said adjustable high-frequency multivibrator includes an enable input, said first frequency divider includes an enable input, said indicator includes a signal input, and said ergometer further comprises:

a work comparison circuit comparing the work performed by said individual with a permissible magnitude and having a first set of inputs, a second set of inputs equal in number to the number of inputs of said first set of inputs, an input and an output, said input being connected to said output of said power supply unit, the inputs of said first set of inputs being respectively connected to corresponding highest bit position outputs of said first multi-digit counter;

a first setting unit setting the permissible magnitude of work performed by said individual and having a set of outputs equal in number to the number of inputs of said second set of inputs of said work comparison circuit, and an input connected to said output of said power supply unit, and the outputs of said set of outputs being respectively connected to corresponding inputs of said second set of inputs of said work comparison circuit;

a power comparison circuit comparing the power developed by said individual to a permissible value and having an input, a first set of inputs equal in number to the number of bit position outputs of said second multi-digit counter, a second set of inputs equal in number to the number of bit position outputs of said second multi-digit counter, and an output, said input being connected to said output of said power supply unit, and the inputs of said first set of inputs being respectively connected to corresponding bit position outputs of said second multi-digit counter;

a second setting unit setting the permissible magnitude of power developed by said individual and having a set of outputs equal in number to the number of inputs of said second set of inputs of said power comparison circuit, and an input connected to said output of said power supply unit, and the outputs of said set of outputs being respectively connected to corresponding inputs of said second plurality of inputs of said power comparison circuit;

a low-frequency multivibrator having a first input, a second input and an output, said first input being connected to said output of said power supply unit;

an OR gate having a first input a first input connected to said output of said power supply unit, a second input connected to said output of said work comparison circuit, a third input connected to said output of said power comparison circuit, and an output connected to said enable input of said adjustable high-frequency multivibrator, to said enable input of said first frequency divider and to said second input of said low frequency multivibrator; and a mixer having a first input connected to said output of said power supply unit, a second input connected to said output of said adjustable high-frequency multivibrator, a third input connected to said output of said low-frequency multivibrator, and an output connected to said signal input of said indicator.

6. An electronic ergometer according to claim 3, wherein said adjustable high-frequency multivibrator includes an enable input, said first frequency divider includes an enable input, said indicator includes a signal input, and said ergometer further comprises:

a work comparison circuit comparing the work performed by said individual with a permissible magnitude and having a first set of inputs, a second set of inputs equal in number to the number of inputs of said first set of inputs, an input and an output, said input being connected to said output of said power supply unit, and the inputs of said first set of inputs being respectively connected to corresponding highest bit position outputs of said first multi-digit counter;

a first setting unit setting the permissible magnitude of work performed by said individual and having a set of outputs equal in number to the number of inputs of said second set of inputs of said work comparison circuit, and an input connected to said output of said power supply unit, and the outputs of said set of outputs being respectively connected to corresponding inputs of said second set of inputs of said work comparison circuit;

a power comparison circuit comparing the power developed by said individual with a permissible magnitude and having an input, a first set of inputs equal in number to the number of outputs of said plurality of outputs of said register, a second set of inputs equal in number to the number of outputs of said set of outputs of said register, and an output, said input being connected to said output of said power supply unit, and the inputs of said first set of inputs being respectively connected to corresponding outputs of said set of outputs of said register;

a second setting unit setting the permissible magnitude of power developed by said individual and having a set of outputs equal in number to the number of inputs of said second set of inputs of said power comparison circuit, and an input connected to said output of said power supply unit, and the outputs of said set of outputs being respectively connected to corresponding inputs of said second set of inputs of said power comparison circuit;

a low-frequency multivibrator having a first input, a second input and an output, said first input being connected to said output of said power supply unit;

an OR gate having a first input connected to said output of said power supply unit, a second input connected to said output of said power comparison circuit, a third input being connected to said output of said work comparison circuit, and an output connected to said enable input of said adjustable high-frequency multivibrator, to said enable input of said first frequency divider and to said second input of said low-frequency multivibrator;

a mixer having a first input connected to said output of said power supply unit, a second input connected to said output of said adjustable high-frequency multivibrator, a third input connected to said output of said low-frequency multivibrator, and an output connected to said signal input of said indicator.

7. An electronic ergometer according to claim 5, further comprising a second OR gate having a first input connected to said output of said power supply unit, a second input connected to said output of said indicator switching unit, a third input connected to said output of said power comparison circuit, and an output connected to said control input of said indicator and to said control input of said power indication permitting unit.

8. An electronic ergometer according to claim 6, further comprising a second OR gate having a first input connected to said output of said power supply unit, a second input connected to said output of said indicator switching unit, a third input connected to said output of said power comparison circuit, and an output connected to said control input of said indicator and to said control input of said power indication permitting unit.

9. An electronic ergometer according to claim 8, wherein said pulse shaper comprises a plurality of threshold elements equal in number to the number of said seismic pickups, each of said threshold elements having a first input connected to said output of said power supply unit, a second input connected to the output of a respective seismic pickup and an output; and an adder having an output connected to said output of said pulse shaper, and a set of inputs equal in number to the number of said threshold elements, said input to said adder being connected to said outputs of said threshold elements.

* * * * *